United States Patent
Carney et al.

(10) Patent No.: US 10,898,412 B2
(45) Date of Patent: Jan. 26, 2021

(54) MECHANICAL FRICTION ENHANCEMENT FOR THREADED CONNECTION INCORPORATING MICRO-THREADS

(71) Applicant: Becton Dickinson and Company Ltd., Dun Laoghaire (IE)

(72) Inventors: Christopher Carney, Clinton, NJ (US); Paul Paia Marici, Piscataway, NJ (US)

(73) Assignee: Becton Dickinson and Company, Ltd., Dun Laoghaire (IE)

( * ) Notice: Subject to any disclaimer, the term of this patent is extended or adjusted under 35 U.S.C. 154(b) by 126 days.

(21) Appl. No.: 16/130,182

(22) Filed: Sep. 13, 2018

(65) Prior Publication Data

US 2019/0008725 A1   Jan. 10, 2019

Related U.S. Application Data

(63) Continuation of application No. 14/278,841, filed on May 15, 2014, now Pat. No. 10,098,816.

(60) Provisional application No. 61/824,172, filed on May 16, 2013.

(51) Int. Cl.
*A61J 1/20* (2006.01)
*F16L 15/06* (2006.01)
*F16L 15/08* (2006.01)
*A61M 39/10* (2006.01)

(52) U.S. Cl.
CPC ........ *A61J 1/2096* (2013.01); *A61M 39/1011* (2013.01); *F16L 15/06* (2013.01); *F16L 15/08* (2013.01); *A61M 2039/1033* (2013.01); *A61M 2039/1044* (2013.01); *Y10T 29/49948* (2015.01)

(58) Field of Classification Search
CPC .............. A61J 1/2096; A61M 39/1011; A61M 2039/1033; A61M 2039/1044; F16L 15/002; F16L 15/004; F16L 15/007; F16L 15/009
USPC ........................................................... 285/92
See application file for complete search history.

(56) References Cited

U.S. PATENT DOCUMENTS

| | | | |
|---|---|---|---|
| 2,355,486 A | 8/1944 | Tinnerman |
| 3,405,831 A | 10/1968 | Hudson |
| 3,741,421 A | 6/1973 | Wittwer |
| 3,876,234 A | 4/1975 | Harms |
| 4,289,248 A | 9/1981 | Lynn |
| 4,360,024 A | 11/1982 | Wallace |
| 4,444,421 A | 4/1984 | Ahlstone |
| 4,452,473 A | 6/1984 | Ruschke |
| 4,629,455 A | 12/1986 | Kanno |

(Continued)

FOREIGN PATENT DOCUMENTS

| | | |
|---|---|---|
| EP | 0158030 A1 | 10/1985 |
| EP | 2056009 A2 | 5/2009 |

(Continued)

*Primary Examiner* — James M Hewitt, II
(74) *Attorney, Agent, or Firm* — The Webb Law Firm (57) ABSTRACT

A medical connector includes a body having a distal end, a proximal end, and a sidewall extending between the distal end and the proximal end, a helical thread extending radially outward from a surface of the sidewall and comprising a crest portion, flank portions, and a root portion with the flank portions connecting the root portion to the crest portion, and at least one micro-thread extending radially outward from the surface of the sidewall. At least a portion of the micro-thread is spaced apart from the helical thread.

15 Claims, 10 Drawing Sheets

(56) References Cited

U.S. PATENT DOCUMENTS

| | | | |
|---|---|---|---|
| 4,735,441 A | 4/1988 | Stephens | |
| 4,770,308 A | 9/1988 | Lynn | |
| 5,106,130 A | 4/1992 | Ellsworth et al. | |
| 5,112,318 A | 5/1992 | Novacek et al. | |
| 5,176,415 A | 1/1993 | Choksi | |
| 5,213,225 A | 5/1993 | King et al. | |
| 5,263,945 A | 11/1993 | Byrnes et al. | |
| 5,312,377 A | 5/1994 | Dalton | |
| 5,462,186 A * | 10/1995 | Ladina | B65D 41/0471 215/218 |
| 5,591,143 A | 1/1997 | Trombley, III et al. | |
| 5,620,427 A | 4/1997 | Werschmidt et al. | |
| 5,651,776 A | 7/1997 | Appling et al. | |
| 5,676,270 A * | 10/1997 | Roberts | B65D 41/0471 215/330 |
| 5,702,374 A | 12/1997 | Johnson | |
| 5,785,357 A | 7/1998 | Foster et al. | |
| 5,855,568 A | 1/1999 | Battiato et al. | |
| 5,871,473 A | 2/1999 | Strauss et al. | |
| 5,984,373 A | 11/1999 | Fitoussi et al. | |
| 6,074,373 A | 6/2000 | Sudo et al. | |
| 6,152,913 A | 11/2000 | Feith et al. | |
| 6,224,588 B1 | 5/2001 | Jentzen | |
| 6,673,059 B2 | 1/2004 | Guala | |
| 6,722,705 B2 | 4/2004 | Korkor | |
| 6,843,513 B2 | 1/2005 | Guala | |
| 6,869,426 B2 | 3/2005 | Ganem | |
| 6,893,056 B2 | 5/2005 | Guala | |
| 7,128,348 B2 | 10/2006 | Kawamura et al. | |
| 7,314,061 B2 | 1/2008 | Peppel | |
| 7,347,458 B2 | 3/2008 | Rome et al. | |
| 7,503,596 B2 | 3/2009 | Rome et al. | |
| 7,523,967 B2 | 4/2009 | Steppe | |
| 7,571,937 B2 | 8/2009 | Patel | |
| 7,618,072 B2 | 11/2009 | Funamura et al. | |
| 7,708,714 B2 | 5/2010 | Connell et al. | |
| 7,722,090 B2 | 5/2010 | Burton et al. | |
| 7,740,288 B2 | 6/2010 | Mantell | |
| 7,845,687 B2 | 12/2010 | Roussie | |
| 7,998,133 B2 | 8/2011 | Fago et al. | |
| 7,998,134 B2 | 8/2011 | Fangrow et al. | |
| 8,038,182 B2 | 10/2011 | Kurimoto et al. | |
| 8,162,897 B2 | 4/2012 | Byrum | |
| 8,262,644 B2 | 9/2012 | Fago et al. | |
| 8,286,936 B2 | 10/2012 | Kitani et al. | |
| 8,287,518 B2 | 10/2012 | Kitani et al. | |
| 8,372,057 B2 | 2/2013 | Cude et al. | |
| 8,372,059 B2 | 2/2013 | Ziman | |
| 2003/0073959 A1 | 4/2003 | Koska | |
| 2003/0155768 A1 | 8/2003 | Hollingsworth et al. | |
| 2004/0238776 A1 | 12/2004 | Peters et al. | |
| 2008/0004600 A1 | 1/2008 | Kitani et al. | |
| 2008/0007060 A1 | 1/2008 | Simpson et al. | |
| 2008/0103485 A1 | 5/2008 | Kruger | |
| 2008/0140020 A1 | 6/2008 | Shirley | |
| 2008/0140055 A1 | 6/2008 | Shirley | |
| 2008/0287919 A1 | 11/2008 | Kimball | |
| 2008/0314856 A1 * | 12/2008 | Penny | B29C 49/06 215/252 |
| 2009/0143746 A1 | 6/2009 | Mudd et al. | |
| 2009/0163859 A1 | 6/2009 | Lloyd et al. | |
| 2009/0177186 A1 | 7/2009 | Delano | |
| 2009/0187166 A1 | 7/2009 | Young | |
| 2010/0022951 A1 | 1/2010 | Ferrera et al. | |
| 2010/0036365 A1 | 2/2010 | Becker | |
| 2010/0089475 A1 | 4/2010 | Tracey | |
| 2010/0152669 A1 | 6/2010 | Rosenquist | |
| 2010/0283238 A1 | 11/2010 | Deighan et al. | |
| 2011/0095528 A1 | 4/2011 | Forberg | |
| 2011/0165020 A1 | 7/2011 | Tryggvason et al. | |
| 2012/0041425 A1 | 2/2012 | Tsunematsu et al. | |
| 2012/0116355 A1 | 5/2012 | Heinz et al. | |
| 2012/0209252 A1 | 8/2012 | Nikitina et al. | |
| 2013/0046255 A1 | 2/2013 | Ziman et al. | |
| 2013/0069365 A1 | 3/2013 | Pokorney | |
| 2013/0076030 A1 | 3/2013 | Fog et al. | |
| 2013/0079754 A1 | 3/2013 | Sheffer | |
| 2013/0103003 A1 | 4/2013 | Capitaine et al. | |

FOREIGN PATENT DOCUMENTS

| | | |
|---|---|---|
| EP | 2174687 A2 | 4/2010 |
| FR | 2863681 A1 | 6/2005 |
| GB | 2353078 A | 2/2001 |
| JP | 5506416 A | 9/1993 |
| JP | 200372793 A | 3/2003 |
| WO | 200814447 A2 | 11/2008 |

* cited by examiner

MECHANICAL FRICTION ENHANCEMENT FOR THREADED CONNECTION INCORPORATING MICRO-THREADS

CROSS-REFERENCE TO RELATED APPLICATION

This application is a continuation of U.S. application Ser. No. 14/278,841, entitled "Mechanical Friction Enhancement for Threaded Connection Incorporating Micro-Threads" filed May 15, 2014, which claims priority to U.S. Provisional Application Ser. No. 61/824,172, filed May 16, 2013, the entire disclosures of each of which are hereby incorporated by reference in their entirety.

BACKGROUND OF THE INVENTION

Field of the Invention

The present invention relates to a connector for enabling fluid transfer between a first fluid container and a second fluid container. More specifically, the invention is directed to a connector having structure to increase friction between threaded connection portions.

Description of Related Art

Many medical connectors comprise a first component having a female luer-lock element that is arranged to be rigidly joined to a corresponding male luer-lock element of a second connector component that is attached to a medical line or other medical connection, for example. The male luer-lock element can thus be freely screwed into and unscrewed from the female luer-lock element. However, once the male luer-lock element has been screwed into the female luer-lock element of the connector, there is a risk that the connector components may be accidentally or inadvertently unscrewed, which could lead to the disconnection of the fluid passage. This may entail a serious contamination risk for a patient and/or any other person in the vicinity of the disconnected medical connector. Such a disconnection risk must especially be avoided when administering toxic fluid, such as cytostatic agents.

In addition, when the friction between the female luer-lock and the male luer-lock is low, there is a tendency for users to over-torque the connection because there is no discernable indication that the connection has been fully tightened. This can lead to breakage of the connectors and/or the containers being joined. This low friction is common for connectors used when administering toxic fluid, such as cytostatic agents for chemotherapy, as such connectors are generally made from plastic or polymeric materials whose hardness and/or surface characteristics result in surfaces having low coefficients of friction.

It is, therefore, desirable to provide a connection for enabling fluid transfer between a first fluid container and a second fluid container that provides not only some resistance to disconnection but also an indication to the user when the connection has been made and is sufficiently tight to proceed with the transfer.

SUMMARY OF THE INVENTION

In one embodiment, a medical connector includes a body having a distal end, a proximal end, and a sidewall extending between the distal end and the proximal end, a helical thread extending radially outward from a surface of the sidewall and comprising a crest portion, flank portions, and a root portion with the flank portions connecting the root portion to the crest portion, and at least one micro-thread extending radially outward from the surface of the sidewall. At least a portion of the micro-thread is spaced apart from the helical thread.

The axial width of the at least one micro-thread may be smaller than the axial width of the root portion of the helical thread and the radial height of the at least one micro-thread from the surface of the sidewall may be less than the radial height of the crest portion of the helical thread from the surface of the sidewall. The micro-thread may extend around the circumference of the body at an angle with respect to an axis extending along the surface of the sidewall from the distal end of the body to the proximal end of the body that is greater than or equal to 0° and less than 180°. The angle may be equal to the helix angle of the helical thread. The radial height of the at least one micro-thread from the surface of the sidewall may taper circumferentially from a first end that forms a sidewall to a second end that is substantially flush with the sidewall of the body.

The medical connector may further comprise a stop extending radially outward from the surface of the sidewall at the proximal end of the connector. The stop may be a solid body or may comprise a plurality of portions separated by gaps. The portions may comprise a top surface, an outer wall, a first side, and a second side.

The radial height of the stop or the portions of the stop from the surface of the sidewall may taper circumferentially from the first end to the second end of the stop such that the first end of the stop has a radial height from the surface of the sidewall that is larger than the radial height of the second end from the surface of the sidewall. Alternatively, or additionally, the maximum axial height of the stop from the proximal end of the body may taper circumferentially from the first end to the second end of the stop such that the first end of the stop has a maximum axial height from the proximal end of the body that is larger than the maximum axial height of the second end from the proximal end of the body. The medical connector may further include a mating connector comprising a body having a distal end, a proximal end, and a sidewall extending between the distal end and the proximal end, and a helical thread extending radially outward from the surface of the sidewall, the helical thread of the mating connector adapted to engage the helical thread of the connector.

In a further embodiment, a method of connecting two fluid containers includes: providing a connector having a helical thread extending radially outward from the surface of the connector, and a mating connector comprising a helical thread extending radially outward from the surface of the mating connector. The connector includes at least one micro-thread extending radially outward from the root portion of the helical thread. The helical thread of the mating connector is engaged with the helical thread of the connector and the mating connector is advanced onto the connector by rotating the mating connector. The at least one micro-thread engages the mating connector such that the friction between the connector and the mating connector is increased when the at least one micro-thread of the connector contacts the helical thread of the mating connector as the mating connector is advanced onto the connector.

The method may further include engaging a stop with the mating connector to stop advancement of the mating connector onto the connector. The connector may have more than one micro-thread and each micro-thread may be sized and positioned such that the increase in friction provided by contact with each successive micro-thread is greater than the increase in friction provided by a previously contacted micro-thread. Further, the first micro-thread that contacts the helical thread of the mating connector may have a smaller surface area than the second micro-thread that is subsequently contacted by the helical thread of the mating connector as the mating connector is advanced on the connector.

In another embodiment, a medical connector includes a body having a distal end, a proximal end, and a generally cylindrical sidewall extending between the distal end and the proximal end, a helical thread extending radially outward from the surface of the sidewall and comprising a crest portion, flank portions, and a root portion with the flank portions connecting the root portion to the crest portion, and a first protrusion extending radially outward from the crest portion of the helical thread.

The connector may further comprise a second protrusion extending radially outward from the sidewall of the body where the circumferential length of the first protrusion is longer than the circumferential length of the second protrusion. The first and second protrusions may include a first end and a second end and the radial height of the protrusion at the first end may be greater than the radial height of the protrusion at the second end. Further, the axial width of the protrusion may be larger at the first end than the axial width of the first protrusion at the second end. The protrusions may be substantially aligned in a longitudinal direction of the body and may have a body that defines a generally teardrop-shaped circumference.

The connector may further comprise a plurality of first protrusions with each first protrusion extending radially outward from the crest portion of the helical thread. The plurality of first protrusions may be circumferentially spaced from each other around the body. In addition, or alternatively, the connector may further comprise a plurality of second protrusions with each second protrusion extending radially outward from the sidewall of the body. The plurality of second protrusions may be circumferentially spaced from each other around the body.

DESCRIPTION OF THE INVENTION

For purposes of the description hereinafter, the terms such as "end", "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting. Further, it is to be understood that the invention may assume various alternative variations and step sequences, except where expressly specified to the contrary.

Figure 1:
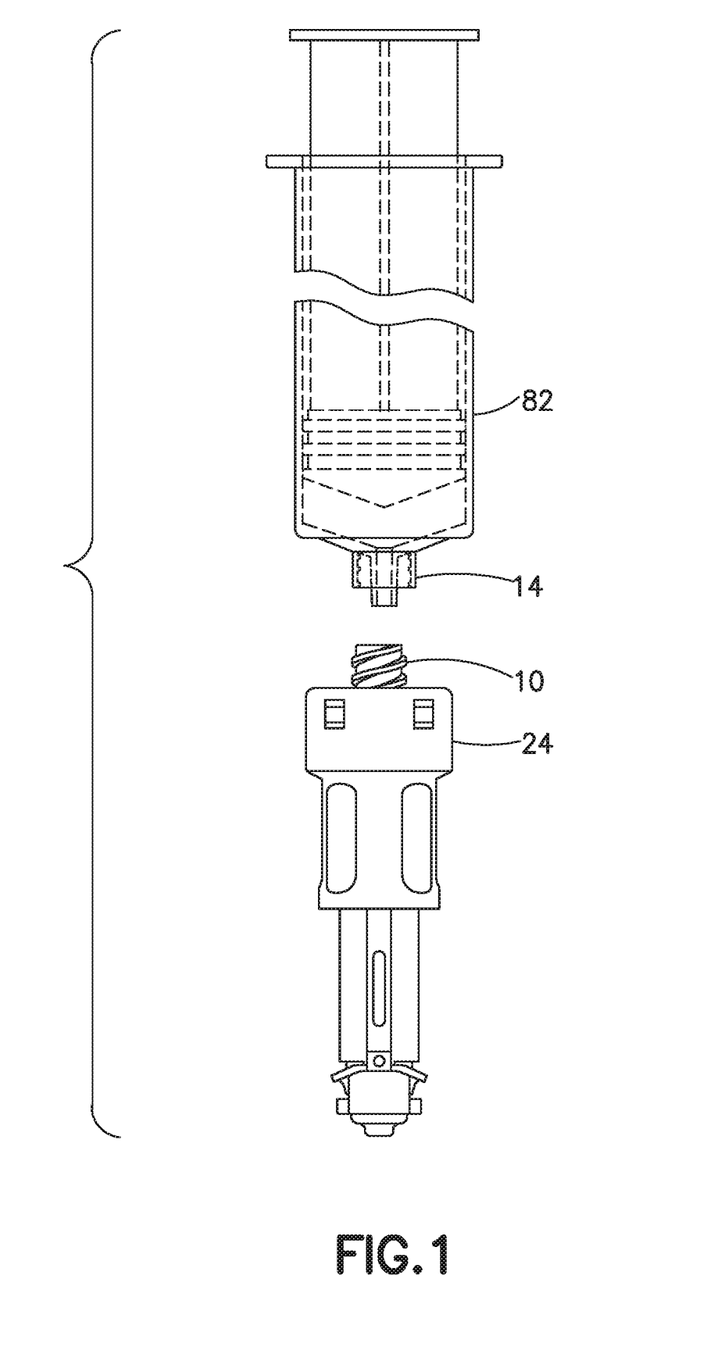
FIG. 1 is a perspective view of a conventional syringe and syringe adapter.
Figure 2:
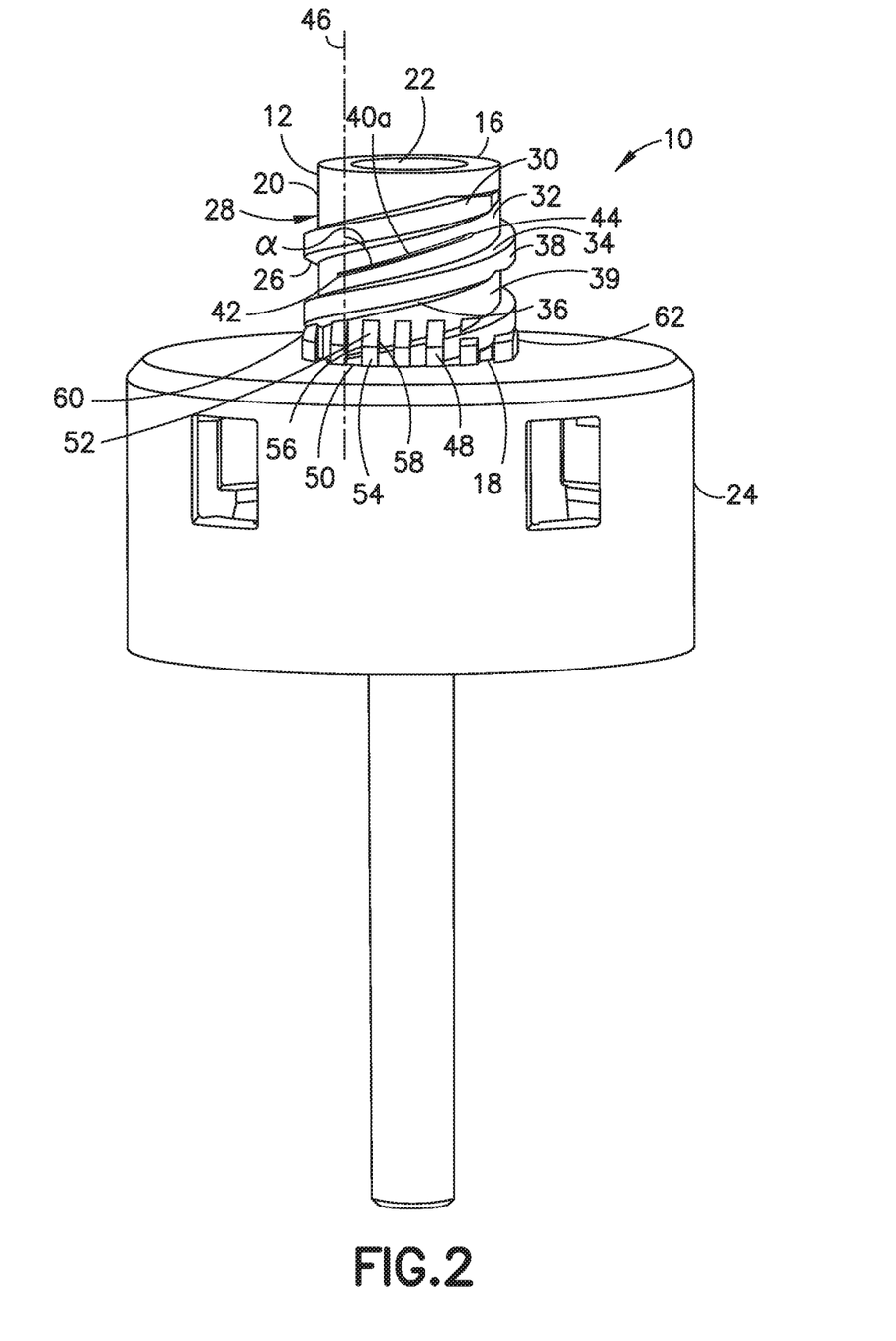
FIG. 2 is a front perspective view of a connector according to one embodiment of the present application.
Figure 3:
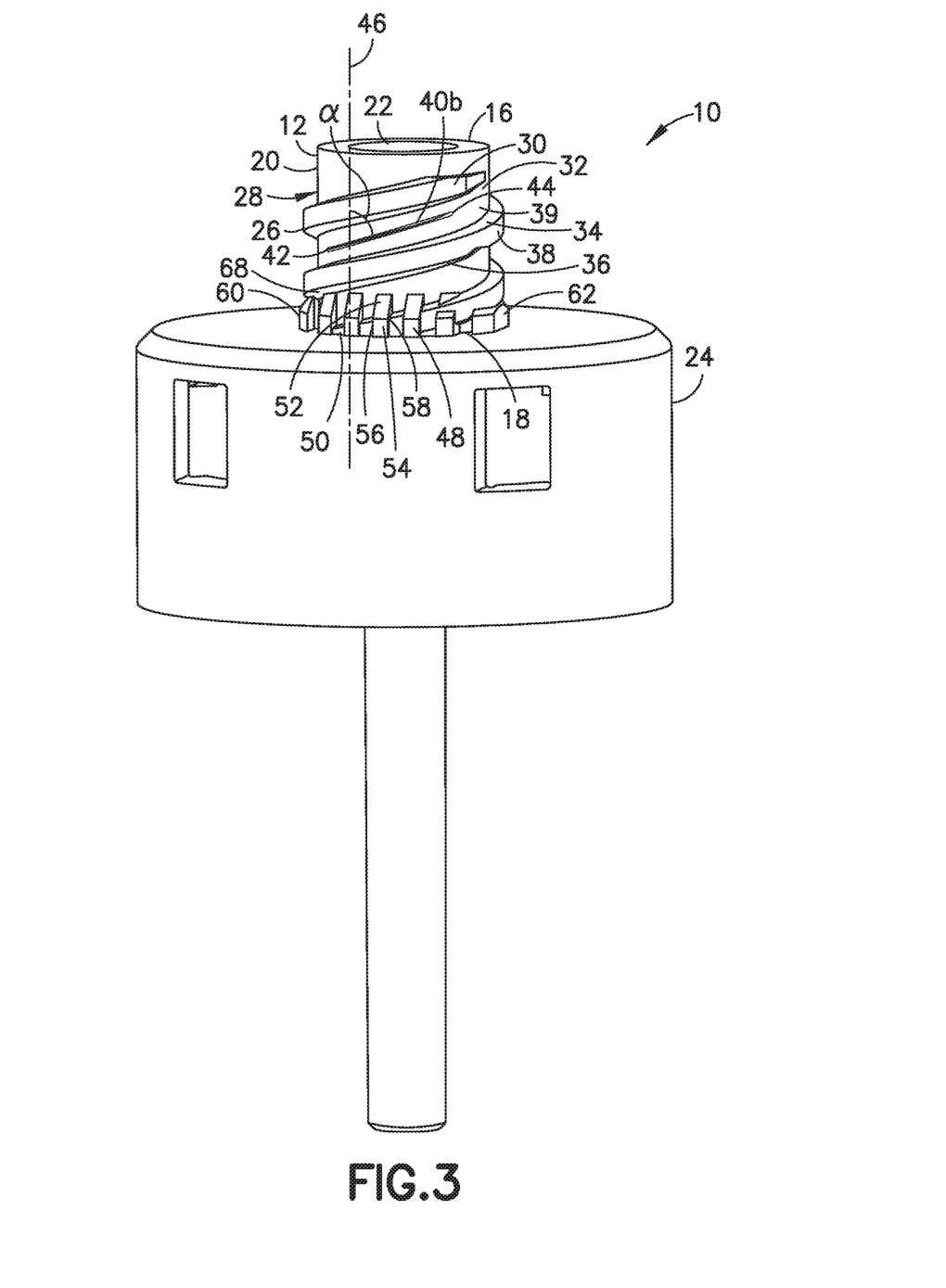
FIG. 3 is a rear perspective view of the connector shown in FIG. 2 according to one embodiment of the present application.
Figure 4:
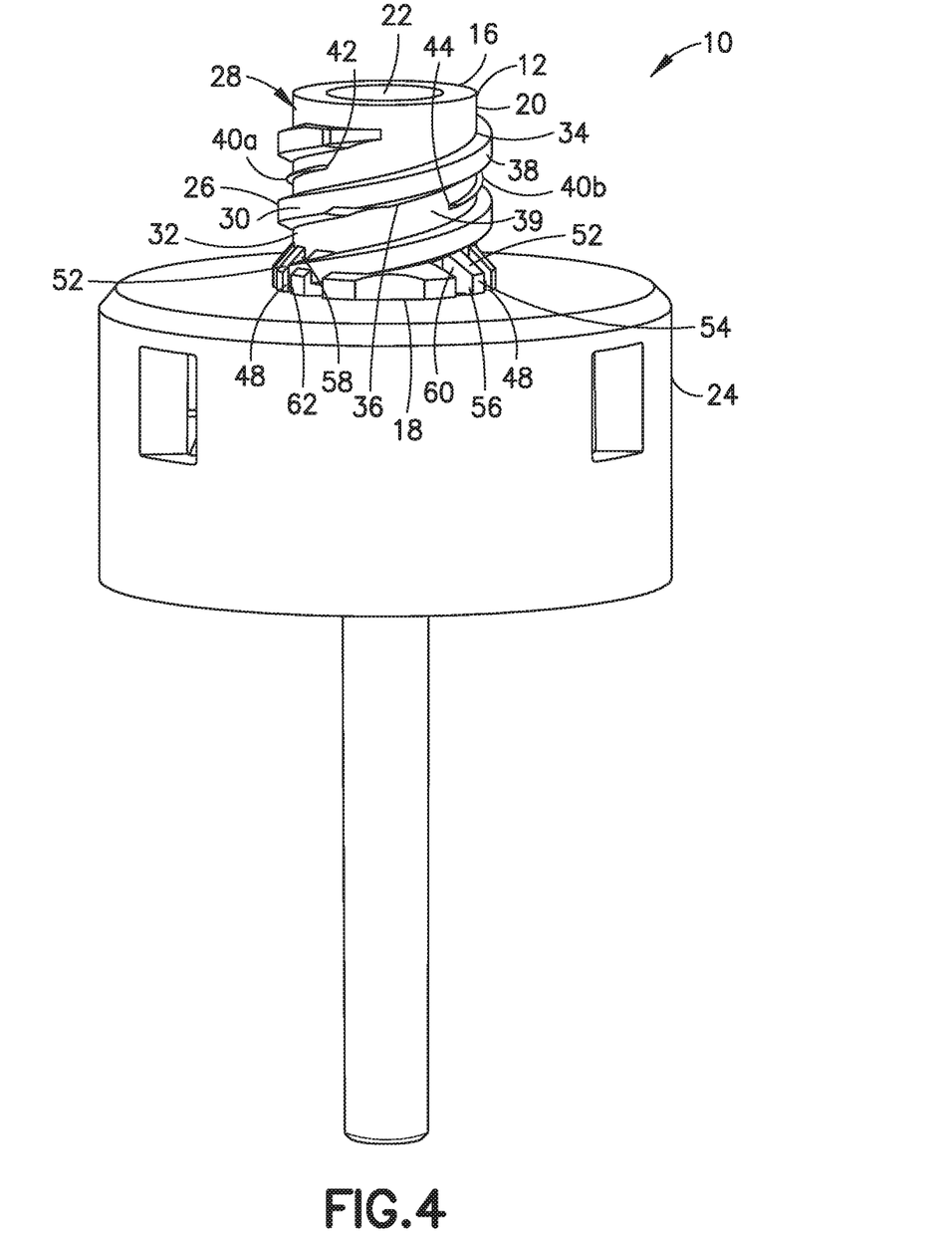
FIG. 4 is a right-side perspective view of the connector shown in FIG. 2 according to one embodiment of the present application.
Figure 5:
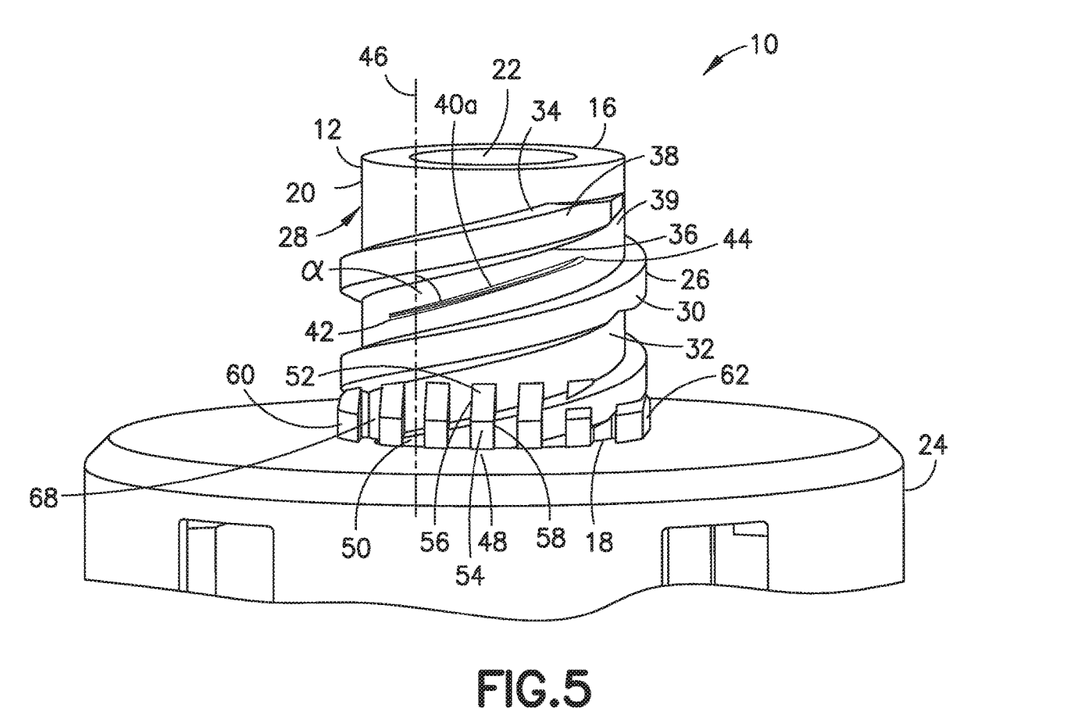
FIG. 5 is an enlarged front perspective view of the connector shown in FIG. 2 according to one embodiment of the present application.
Figure 6:
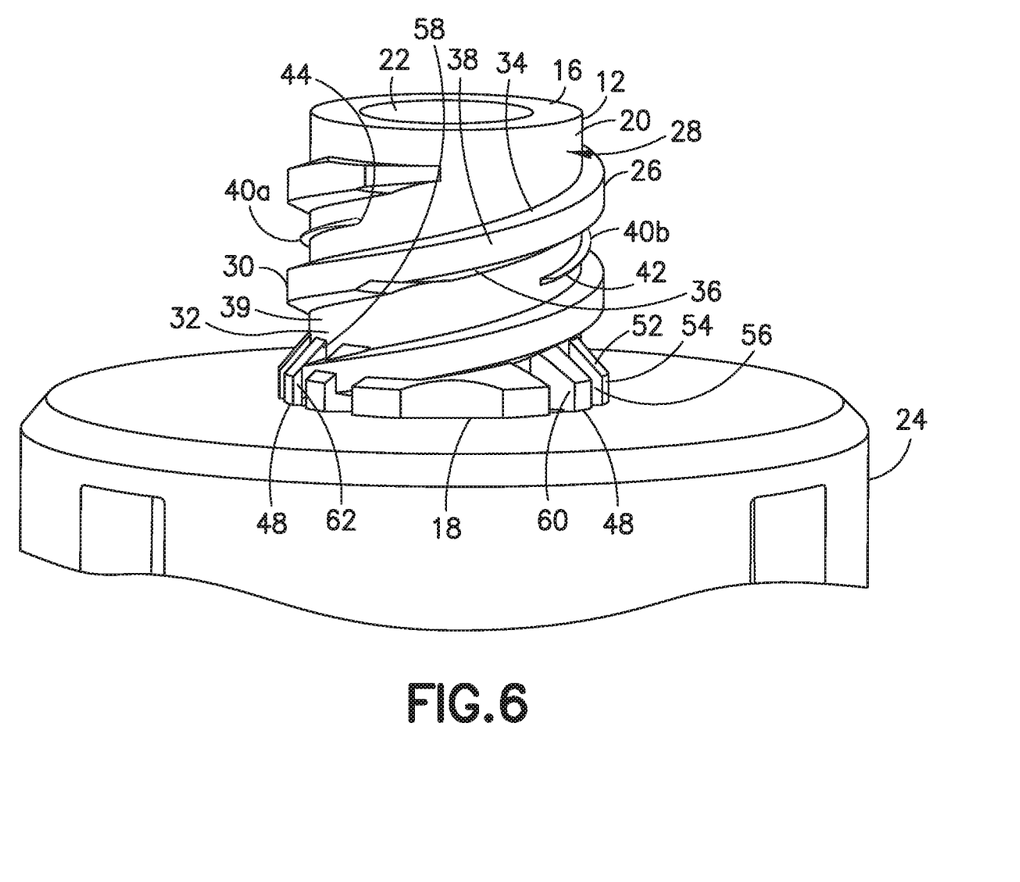
FIG. 6 is an enlarged right-side perspective view of the connector shown in FIG. 2 according to one embodiment of the present application.

Referring to FIG. 1, a conventional syringe 82 and syringe adapter 24 are shown. The syringe 82 includes a male luer-lock connector that is configured to be secured to a corresponding female luer-lock connector of the syringe adapter 24. The syringe adapter 24 may be a BD PhaSeal™ Injector commercially available from Becton, Dickinson and Company. The syringe adapter 24 forms part of a closed system transfer device that enables a closed transfer of drugs between containers.

One embodiment of the present invention is directed to a connector 10 for fluidly connecting a first fluid container to a second fluid container to allow the fluid in one of the first or second fluid containers to pass into the other of the first or second fluid container. For example, the connector 10 may be utilized in connection with the syringe adapter 24 shown in FIG. 1. A "fluid container" as used herein, is intended to mean any vessel that can at least temporarily contain a fluid, including, but not limited to, a vial, a medical line, a tube, or an infusion fluid container, such as an infusion bottle or an infusion bag, a syringe, or other device.

As shown in FIGS. 2-7, the connector 10 includes a body 12 having a distal end 16, a proximal end 18, and a sidewall 20 extending between the distal end 16 and the proximal end 18 and defining a central lumen 22. The sidewall 20 may be generally cylindrical, although other suitable shapes may be utilized. The connector 10 may be a female luer-lock connector, although other suitable connector arrangements may be utilized. The proximal end 18 of the body 12 of the connector 10 may be attached directly to a first fluid container or may extend from an additional connection portion that connects directly to the fluid container to provide a fluid connection between the first fluid container and the central lumen 22 of the connector 10. In the embodiment shown in FIGS. 2-7, the body 12 of the connector 10 extends from a needle holder of a syringe adapter, such as the syringe adapter 24 shown in FIG. 2. An inner surface of the needle holder may include a projection that cooperates with a body of the syringe adapter 24 to form a ratchet-type connection such that the needle holder is generally free to rotate relative to the body of the syringe adapter 24 in a first direction, but is generally restricted from such relative rotation when rotated in a second, opposite direction.

The body 12 of the connector 10 includes external threads 26 extending radially outward from the external surface 28 of the sidewall 20 and proceeding in a spiral fashion from the distal end 16 to proximal end 18 of the body 12. In the embodiment shown, the body 12 includes two external threads 26, although one or more threads may be provided. The external threads 26 each comprise flank portions 34, 36, a crest portion 38, and a root portion 39. The crest portion 38 and the flank portions 34, 36 together define a helical rib 30 and the root portion 39 and the flank portions 34, 36 together define a helical groove 32. The crest portion 38 of the external threads 26 extends radially a distance from the external surface 28 of the sidewall 20. The helical ribs 30 may have any suitable cross-sectional shape, including but not limited to, square, rounded, and trapezoidal. In the embodiment shown in FIGS. 2-7, the helical rib 30 has a generally trapezoidal cross-section with the crest portion 38 a distance from the external surface 28 of the sidewall 20 and substantially parallel to the external surface 28 of the sidewall 20. The two flank portions 34, 36 extend from the crest portion 38 inward toward the external surface 28 of the sidewall 20. The angle between the flank portions 34, 36 and the root portion 39 is greater than 90° as is the angle between the flank portions 34, 36 and the crest portion 38. The shape of the helical groove 32 is defined by the flank portions 34, 36 and the root portion 39. In the embodiment shown in FIGS. 2-7, the helical groove 32 has a trapezoidal shape.

The connector 10 has at least one micro-thread 40a, 40b extending radially outward from the root portion 39 of the external thread 26 such that it is generally disposed within the helical groove 32. Thus, the micro-thread 40a, 40b is spaced apart from the external thread 26. The micro-thread 40a, 40b has a radial height from the external surface 28 of the sidewall 20 that is less than the radial height of the crest portion 38 of the external thread 26 from the external surface 28 from the sidewall 20 and a width in the axial direction that is less than the width of the root portion 39 in the axial direction.

Figure 7:
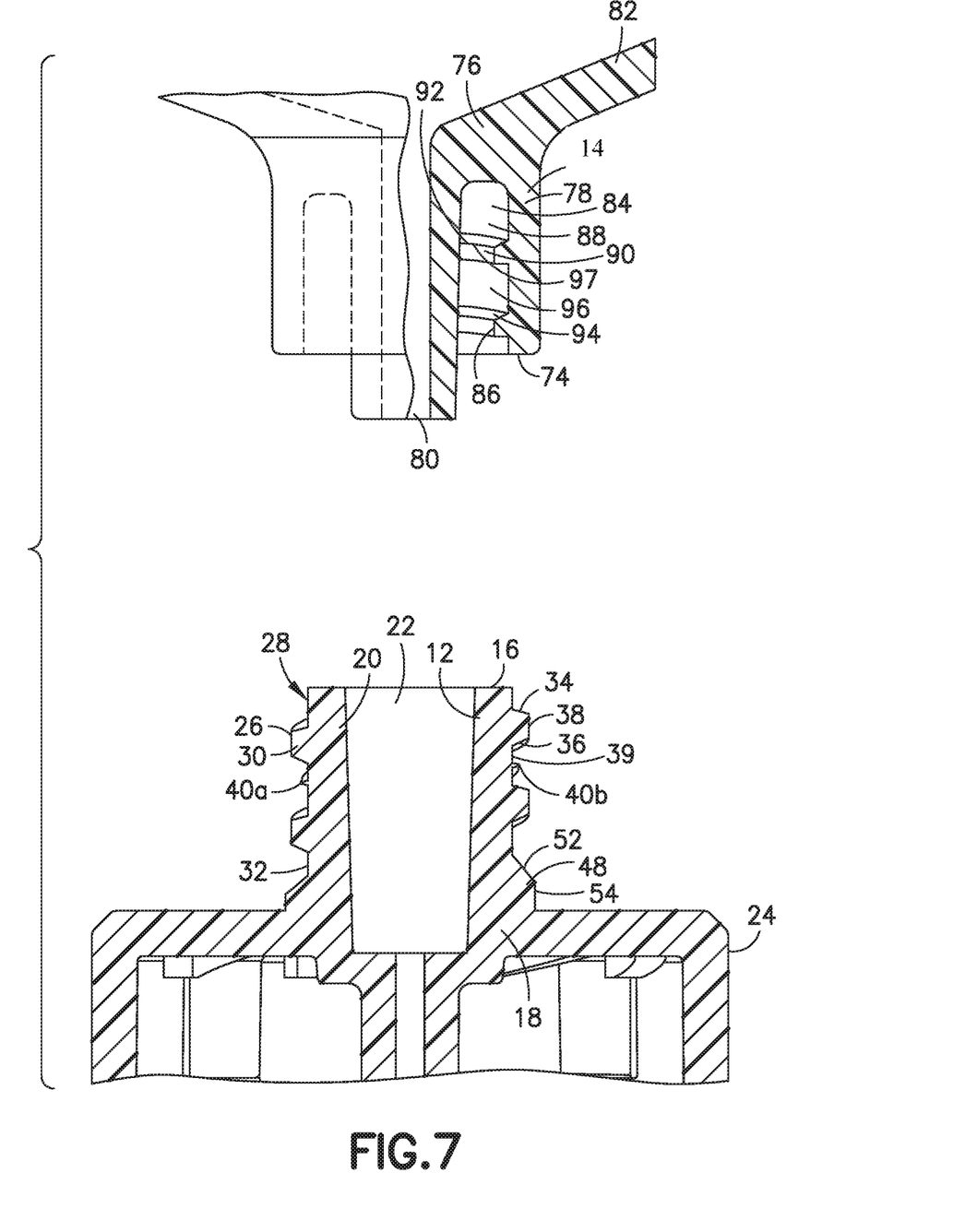
FIG. 7 is a partial cross-sectional view of the connector shown in FIG. 2 and a mating connector in a disconnected state according to one embodiment of the present application.

In the embodiment shown in FIGS. 2-7, two micro-threads 40a, 40b are disposed in the helical groove 32 on opposite sides of the body 12 of the connector 10. The micro-threads 40a, 40b extend for approximately 90° around the circumference of the sidewall 20 of the body 12 in a direction substantially parallel to the flank portions 34, 36 of the external threads 26. This results in the micro-threads 40a, 40b being at an angle α with respect to an axis 46 extending along the external surface 28 of the sidewall 20 from the distal end 16 of the body 12 to the proximal end 18 of the body 12. In the illustrated embodiment, micro-threads 40a, 40b extend at an angle that is less than 90° and is substantially equal to the helix angle of the external threads 26. Also, as can be seen in FIG. 7, the micro-threads 40a, 40b have a triangular cross-section.

As can be appreciated by a person skilled in the art, the embodiment described above, and shown in FIGS. 2-7, is only one embodiment of the present invention. The micro-threads 40a, 40b may be present in any number, take any shape, size, and cross-section, and be oriented in any direction within the helical groove 32 as long as they extend from the root portion 39 into the helical groove 32 and act to increase friction when the connector 10 is threaded into a mating connector 14 as will be described later.

The micro-threads 40a, 40b may extend from a first end 42 to a second end 44 at any angle α with respect to an axis 46 extending along the external surface 28 of the sidewall 20 from the distal end 16 of the body 12 to the proximal end 18 of the body 12. The angle α may be greater than or equal to 0° and less than 180°. For example, the micro-threads 40a, 40b may extend in the axial direction within the helical groove 32 such that they are parallel to the axis 46, i.e., at 0°, and substantially perpendicular to the helical rib 30.

The micro-threads 40a, 40b may have any suitable cross-section, including but not limited to, triangular, rounded, square, rectangular, and trapezoidal.

The micro-threads 40a, 40b may extend any suitable distance around the circumference of the external surface 28 of the sidewall 20 from a short distance of only a few degrees around the sidewall 20 to the full distance, 360°, around the circumference of the sidewall 20.

The micro-threads 40a, 40b may have an axial width that is substantially smaller than the axial width of the root portion 39 of the external thread 26, an axial width that is nearly equal to the axial width of the root portion 39 of the external thread 26, or an axial width that lies between.

The maximum radial height of any portion of the micro-threads 40a, 40b from the external surface 28 of the sidewall 20 is less than the maximum height of any portion of the helical rib 30a, 30b from the external surface 28 of the sidewall 20.

In addition, the radial height of the micro-threads 40a, 40b from the exterior surface 28 of the sidewall 20 may taper circumferentially from the first end 42 to the second end 44. Accordingly, the radial height of the micro-threads 40a, 40b may decrease from the first end 42 to the second end 44 such that the thinner or smaller portion of the micro-thread 40a, 40b is oriented on the higher side of the helix angle defined by the external threads 26. Thus, the first end 42 of the micro-thread 40a, 40b may form a sidewall while the second end 44 of the micro-thread 40a, 40b may be nearly flush with the external surface 28 of the sidewall 20.

As shown in FIGS. 2-7, at least one stop 48 may be superimposed over a portion of the proximal-most end 50 of at least one of the helical ribs 30. The stop 48 comprises a number of portions separated by gaps in which the helical rib 30 is visible. Each portion of the stop 48 extends radially outward from the external surface 28 of the sidewall 20 and comprises a top surface 52, an outer wall 54 that extends from the top surface 52 to the proximal end 18 of the body 12 of the connector 10, a first side 56, and a second side 58. The first end 60 of the stop 48 is adjacent the proximal-most end 50 of one of the helical ribs 30 and the stop 48 is generally disposed within the proximal-most end 68 of the helical groove 32.

The top surface 52 of each portion of the stop 48 is angled away from the external surface 28 of the sidewall 20 toward the proximal end 18 of the body 12 such that the axial height of the portion of the stop 48 from the top surface 52 adjacent the sidewall 20 to the proximal end 18 of the body 12 is greater than the axial height of the portion of the stop 48 from the top surface 52 adjacent the outer wall 54 of the portion of the stop 48 to the proximal end 18 of the body 12. In the embodiment shown in FIGS. 2-8, the top surface 52 of each portion of the stop 48 extends from the external surface 28 of the sidewall 20 at an approximately 45° angle.

The outer wall 54 of each portion of the stop 48 extends from the top surface 52 of the portion of the stop 48 to the proximal end 18 of the body 12 at any suitable angle. In the embodiment shown in FIGS. 2-7, the outer wall 54 of each portion of the stop 48 extends from the top surface 52 of the portion of the stop 48 to the proximal end 18 of the body 12 such that the outer wall 54 is substantially parallel to the external surface 28 of the sidewall 20. This results in the first side 56 and the second side 58 of each portion of the stop 48 having a trapezoidal shape in the illustrated embodiment.

The stop 48 may alternatively be a single body in which the portions shown in the figures are continuously connected to form the single body.

While the stop 48 has been described and is shown in the figures as having portions or a single body with an angled top surface 52 and trapezoidal sides 56, 58, it can be appreciated by a person skilled in the art that the stop 48 may take any overall shape as long as it extends radially from the external surface 28 of the sidewall 20.

The portions of the stop 48, or the body 12 of the stop 48, if it is a single body, may have a circumferential taper such that the maximum radial height of the first end 60 of the stop 48 from the external surface 28 of the sidewall 20 is greater than the maximum radial height of the second end 62 of the stop 48 from the external surface 28 of the sidewall 20. Thus, the outer walls 54 of the portions of the stop 48, or the outer wall 54 of the stop 48, if it is a single body, forms a wedge shape in the circumferential direction. For example, the first end 60 of the stop 48 may form a sidewall while the second end 62 of the stop 48 may be substantially flush with the external surface 28 of the sidewall 20.

The maximum axial height of the top surface 52 of the portions of the stop 48, or the top surface of the stop 48, if it is a single body, from the proximal end 18 of the body 12, may taper from the first end 60 of the stop 48 to the second end 62 of the stop 48. The maximum axial height of the top surfaces 52 of the portions of the stop 48, or the top surface of the stop 48, if it is a single body, from the proximal end 18 of the body 12 at the first end 60 of the stop 48, is greater than the maximum axial height of the top surfaces 52 of the portions of the stop 48, or the top surface of the stop 48, if it is a single body, from the proximal end 18 of the body 12 at the second end 62 of the stop 48. This results in the top surfaces 52 of the portions of the stop 48, or the top surface of the stop 48, if it is a single body, forming a wedge shape in the axial direction.

The connector 10 is configured to be secured to and mate with a mating connector 14 that includes a body 72 having a distal end 74, a proximal end 76, and a generally cylindrical sidewall 78 extending between the distal end 74 and the proximal end 76 and defining a central lumen 80. The mating connector 14 may be a male luer-lock connector, although other suitable mating connectors may be utilized. The proximal end 76 of the body 72 of the mating connector 14 may be attached directly to a first fluid container or may extend from an additional connection portion that connects directly to the fluid container to provide a fluid connection between the first fluid container and the central lumen 80 of the body 72 of the mating connector 14. In the embodiment shown in FIGS. 1 and 7, the body 72 of the mating connector 14 extends from a syringe such as the one shown in FIG. 1.

The body 72 of the mating connector 14 includes internal threads 84 extending radially outward from the internal surface 86 of the sidewall 78 and proceeding in a spiral fashion from the distal end 74 to proximal end 76 of the body 72. In the embodiment shown, the body 72 includes two internal threads 84, although one or more threads may be provided. The internal threads 84 each comprise flank portions 92, 94, a crest portion 96, and a root portion 97. The crest portion 96 and the flank portions 92, 94 together define a helical rib 88 and the root portion 97 and the flank portions 92, 94 together define a helical groove 90. The crest portion 96 of the internal threads 84 extends radially a distance from the internal surface 86 of the sidewall 78. The helical rib 88 may have any suitable cross-sectional shape, including but not limited to, square, rounded, and trapezoidal. The internal threads 84 are shaped and sized to engage the external threads 26 of the connector 10 so that the body 72 of the mating connector 14 can be threaded onto the body 12 of the connector 10 and tightened to form the connection.

In the embodiment shown in FIG. 7, the helical ribs 88 have a generally trapezoidal cross-section with the crest portion 96 a distance from the internal surface 86 of the sidewall 78 and substantially parallel to the internal surface 86 of the sidewall 78. The two flank portions 92, 94 extend from the crest portion 96 inward toward the internal surface 86 of the sidewall 78. The angle between the flank portions 92, 94 and the root portion 97 is greater than 90° as is the angle between the flank portions 92, 94 and the crest portion 96. The shape of the helical groove 90 is defined by the flank portions 92, 94 and the root portion 97 of the internal threads 84. In the embodiment shown in FIG. 7, the helical groove 90 has a trapezoidal shape.

When a user of the connector 10 desires to make the connection, the mating connector 14 is threaded onto the connector 10, such that the internal threads 84 of the mating connector 14 engage the external threads 26 of the connector 10. As the user continues to advance the mating connector 14 onto the connector 10, the micro-threads 40a, 40b of the connector 10 engage the internal threads 84 of the mating connector 14 resulting in increased friction between the connector 10 and the mating connector 14. The user must then apply increased torque to continue to advance the mating connector 14 onto the connector 10. This provides an indication to the user that the connection is being made and that the connection is being tightened. The friction may continue to increase as the mating connector 14 is advanced onto the connector 10 when the internal threads 84 of the mating connector 14 contact additional micro-threads 40a, 40b until the distal-most end of the threads 84 of the mating connector 14 contact the stop 48 at the proximal end 18 of the body 12 of the connector 10. As the user continues to apply torque to the mating connector 14, the distal-most end of the internal thread 84 of the mating connector 14 is increasingly engaged in a wedging manner by the stop 48.

As will be appreciated by a person skilled in the art, the number, size, shape, and orientation of the micro-threads 40a, 40b is chosen to provide the desired amount of friction during connection and, if desired, chosen to increase or decrease the additional friction that is provided as the mating connector 14 is advanced onto the connector 10. The friction provided is directly proportional to the surface area of the micro-thread 40a, 40b that contacts the helical rib 88 of the internal thread 84 of the mating connector 14 as the mating connector 14 is advanced onto the connector 10. Thus, by increasing the number, circumferential length, axial length, and/or the radial height from the external surface 28 of the sidewall 20 of the micro-threads 40a, 40b as their distance from the distal end 16 of the body 12 increases, the friction between the mating connector 14 and the connector 10 can be gradually increased as the mating connector 14 is advanced onto the connector 10. This gives the user a feeling that the connection is constantly getting tighter and helps to avoid over-tightening of the connection.

Also, providing the micro-threads 40a, 40b with a circumferential taper of the radial height of the micro-thread 40a, 40b from the external surface 28 of the sidewall 20, i.e., a decrease in radial height from the first end 42 to the second end 44 of the micro-thread 40a, 40b, acts to resist disconnection of the connector 10 with the mating connector 14. The circumferential taper from the first end 42 of the micro-thread 40a, 40b to the second end 44 of micro-thread 40a, 40b allows the internal threads 84 of the mating connector 14 to advance over the micro-thread 40a, 40b as the mating connector 14 is threaded onto the connector 10 and first contacts the second end 44 of the micro-thread 40a, 40b. However, the first end 42 of the micro-thread 40a, 40b, which takes the form of a sidewall that extends from the exterior surface 28 of the sidewall 20 of the body 12 of the connector 10, acts as a barb to resist disconnection. In other words, the second end 44 of the micro-thread 40a, 40b may be about flush with the sidewall 20 of the body 12, which allows the mating connector 14 to be threaded onto the connector 10. The micro-thread 40a, 40b increases in radial height as it extends circumferentially from the second end 44 to the first end 42 of the micro-thread 40a, 40b such that the first end 42 defines a sidewall that will engage and bite into the internal threads 84 of the mating connector 14 if a user attempts to unthread the mating connector 14 from the connector 10.

Thus, the engagement of both the micro-threads 40a, 40b and the stop 48 of the connector 10 with the internal threads 84 of the mating connector 14 results in increased friction as the mating connector 14 is advanced onto the connector 10. This increased friction and corresponding increase in torque to make the connection provide an indication to the user that the connection between the connector 10 and the mating connector 14 is being secured. The increased feeling of tightness that is transferred to the user encourages the user to tighten and discourages the user from over-tightening of the connection which can result in breakage of the mating connector 14 or the connector 10. In addition, the increased friction and optional circumferential taper of the micro-threads 40a, 40b make the connection more resistant to disconnection than a connection that merely utilizes corresponding internal and external threads and the inherent frictional properties of the material.

While the discussion and figures have described the micro-threads 40a, 40b and the stop 48 in conjunction with the body 12 of the connector 10, it can be appreciated by a person skilled in the art that the same result may be achieved in the same manner by incorporating the micro-threads 40a, 40b and the stop 48 into the threaded portion of the mating connector 14.

Figure 8:
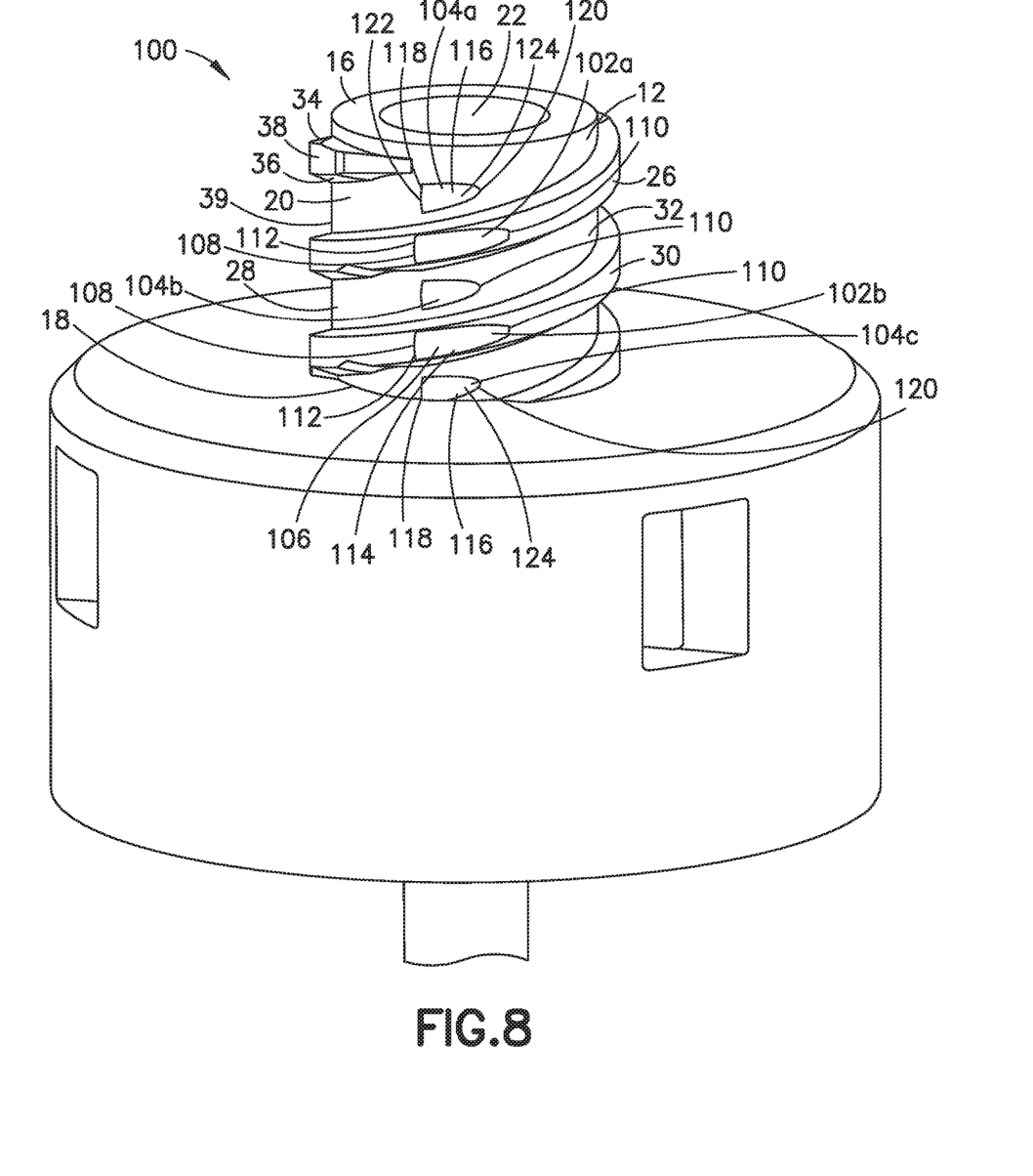
FIG. 8 is a front perspective view of a connector according to a further embodiment of the present application.
Figure 9:
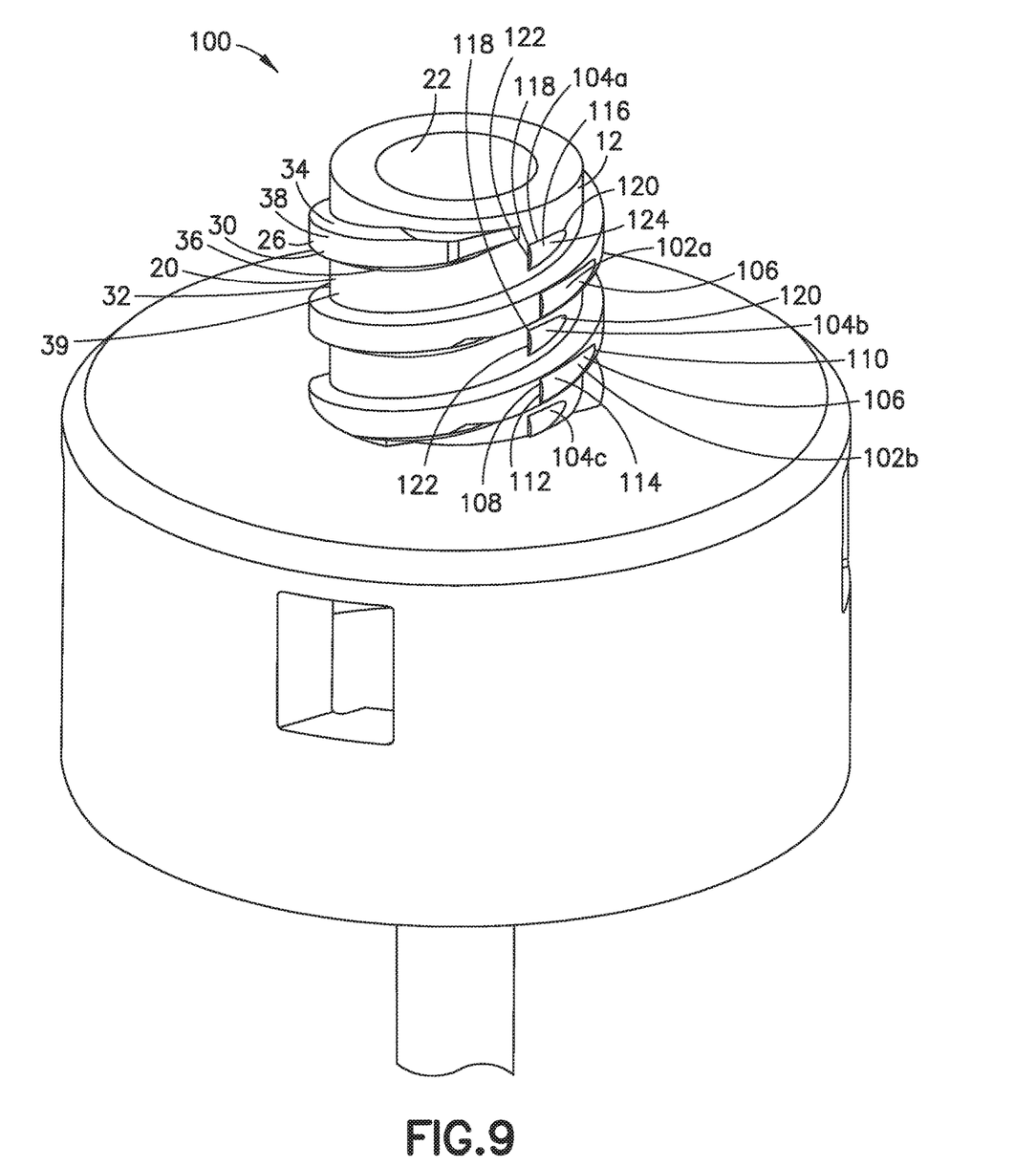
FIG. 9 is a front-right perspective view of the connector shown in FIG. 8.
Figure 10:
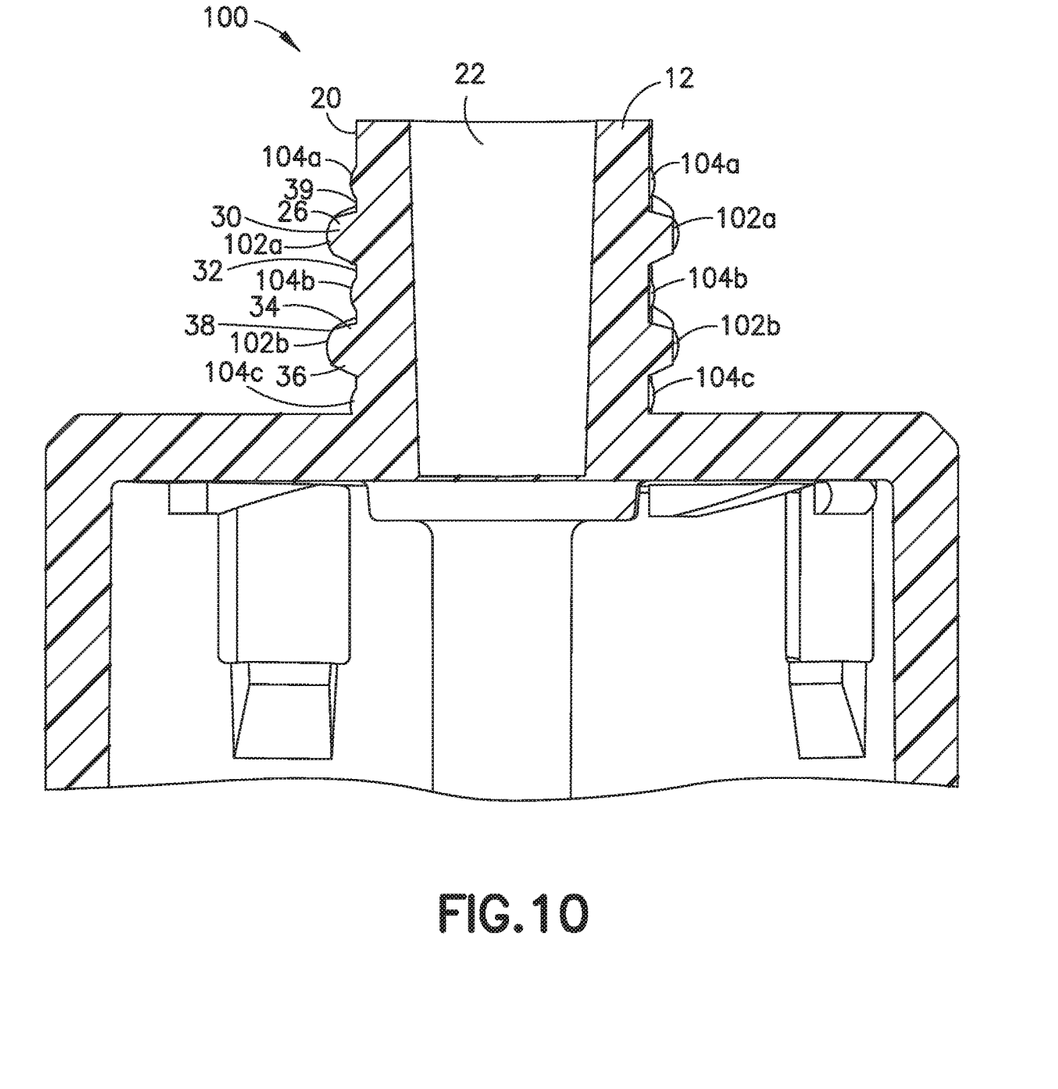
FIG. 10 is a cross-sectional view of the connector shown in FIG. 8.

Referring to FIGS. 8-10, a further embodiment of a connector 100 for fluidly connecting a first fluid container to a second fluid container is shown. The connector 100 is similar to the connector 10 shown in FIGS. 2-7 and described above except for the differences described below. Like reference numerals will be used for like elements. Rather than providing the micro-threads 40a, 40b, the connector 100 includes protrusions 102a, 102b positioned on the crest portions 38 of the external threads 26. The protrusions 102a, 102b each include a body 106 having a first end 108 and a second end 110. The body 106 of each protrusion 102a, 102b extends radially outward from the crest portions 38 of the external threads 26 of the connector 100 and defines a generally teardrop-shaped circumference. The first end 108 of each protrusion 102a, 102b defines an end wall 112 that extends about perpendicular from the crest portions 38 of the external threads 26. The end wall 112 of each protrusion 102a, 102b is generally planar and semi-spherical or semi-elliptical in shape, although other suitable shapes for the end wall 112 may be utilized. In particular, the end wall 112 may have a shape defined by a circular segment, i.e., a portion of a circle that is cut off from the rest of the circle by a secant and excluding the circle's center. Each protrusion 102a, 102b defines an exterior surface 114 that is curved or arc-shaped. The body 106 of each protrusion 102a, 102b tapers in a radial and longitudinal direction. Accordingly, the first end 108 of the body 106 of each protrusion 102a, 102b has a radial height that is larger than at the second end 110 of the body 106. Further, the first end 108 of the body 106 is wider in a longitudinal direction of the connector 100 than at the second end 110 of the body 106.

The connector 100 also includes protrusions 104a, 104b, 104c positioned on the sidewall 20 or root portion 39 of the body 12 of the connector 100. The protrusions 104a, 104b each include a body 116 having a first end 118 and a second end 120. The body 116 of each protrusion 104a, 104b, 104c extends radially outward from the sidewall 20 and defines a generally teardrop-shaped circumference. The first end 118 of each protrusion 104a, 104b, 104c defines an end wall 122 that extends about perpendicular from the sidewall 20 of the connector 100. The end wall 122 of each protrusion 104a, 104b, 104c is generally planar and semi-spherical or semi-elliptical in shape, although other suitable shapes for the end wall 122 may be utilized. In particular, the end wall 122 may have a shape defined by a circular segment, i.e., a portion of a circle that is cut off from the rest of the circle by a secant and excluding the circle's center. Each protrusion 104a, 104b, 104c defines an exterior surface 124 that is curved or arc-shaped. The body 116 of each protrusion 104a, 104b, 104c tapers in a radial and longitudinal direction. Accordingly, the first end 118 of the body 116 of each protrusion 104a, 104b, 104c has a radial height that is larger than at the second end 120 of the body 116. Further, the first end 118 of the body 116 is wider in a longitudinal direction of the connector 100 than at the second end 120 of the body 116.

The protrusions 102a, 102b, 104a, 104b, 104c are generally aligned with each other in a longitudinal direction of the connector 100. The protrusions 102a, 102b have a circumferential length that is larger than a circumferential length of the protrusions 104a, 104b, 104c. Further, the connector 100 is shown with two protrusions 102a, 102b on the crest portion 38 of the external threads 26 and three protrusions 104a, 104b, 104c on the sidewall 20. However, the connector 100 may be provided with one or more of each of the protrusions 102a, 104a. In particular, the connector 100 may only include the protrusions 102a, 102b on the crest portion 38 of the external threads 26 or may only include the protrusions 104a, 104b, 104c on the sidewall 20. Further, the connector 100 may include one or more sets of protrusions 102a, 102b, 104a, 104b, 104c that are spaced apart from each other around the circumference of the connector 100. In one embodiment, the connector includes two sets of protrusions 102a, 102b, 104a, 104b, 104c with one set positioned 180° from the other set around the circumference of the connector 100. A maximum radial height of any portion of the protrusions 102a, 102b, 104a, 104b, 104c from the external surface 28 of the sidewall 20 or from the crest portion 38 of the external threads 26 is less than the maximum height of any portion of the helical rib 30a, 30b from the external surface 28 of the sidewall 20, although other suitable radial heights may be utilized.

When a user of the connector 100 desires to make the connection, the mating connector 14 is threaded onto the connector 100 in the same manner as described above in connection with the connector 10 shown in FIGS. 2-7. As the user advances the mating connector 14 onto the connector 100, the protrusions 102a, 102b, 104a, 104b, 104c engage the internal threads 84 of the mating connector 14 resulting in increased friction between the connector 100 and the mating connector 14. The user must then apply increased torque to continue to advance the mating connector 14 onto the connector 100. This provides an indication to the user that the connection is being made and that the connection is being tightened. As will be appreciated by a person skilled in the art, the number, size, shape, and orientation of the protrusions 102a, 102b, 104a, 104b, 104c is chosen to provide the desired amount of friction during connection and, if desired, chosen to increase or decrease the additional friction that is provided as the mating connector 14 is advanced onto the connector 100. The friction provided is directly proportional to the surface area of the protrusions 102a, 102b, 104a, 104b, 104c that contacts the helical rib 88 of the internal thread 84 of the mating connector 14 as the mating connector 14 is advanced onto the connector 100.

Providing the protrusions 102a, 102b, 104a, 104b, 104c with a circumferential taper of the radial height of the protrusions 102a, 102b, 104a, 104b, 104c from the external surface 28 of the sidewall 20, i.e., a decrease in radial height from the first end 108, 118 to the respective second end 110, 120 of the protrusions 102a, 102b, 104a, 104b, 104c, acts to resist disconnection of the connector 100 with the mating connector 14. The circumferential taper from the first end 108, 118 of the protrusions 102a, 102b, 104a, 104b, 104c to the respective second end 110, 120 of the protrusions 102a, 102b, 104a, 104b, 104c allows the internal threads 84 of the mating connector 14 to advance over the protrusions 102a, 102b, 104a, 104b, 104c as the mating connector 14 is threaded onto the connector 100 and first contacts the second ends 110, 120 of the protrusions 102a, 102b, 104a, 104b, 104c. However, the first ends 108, 118 of the protrusions 102a, 102b, 104a, 104b, 104c, which defines respective end walls 112, 122, acts as a barb to resist disconnection.

While the discussion and figures have described the protrusions 102a, 102b, 104a, 104b, 104c in conjunction with the connector 100, it can be appreciated by a person skilled in the art that the same result may be achieved in the same manner by incorporating the protrusions 102a, 102b, 104a, 104b, 104c into the threaded portion of the mating connector 14.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. A medical connector for enabling fluid transfer between a first medical device and a second medical device comprising:
 a body having a distal end, a proximal end, and a sidewall extending between the distal end and the proximal end;
 a helical thread extending radially outward from a surface of the sidewall and comprising a crest portion, flank portions, and a root portion, the flank portions connecting the root portion to the crest portion; and
 a first protrusion extending radially outward from the crest portion of the helical thread,
 wherein the first protrusion includes a body having a first end and a second end, the first end being wider in a longitudinal direction of the body of the first protrusion than the second end, and
 wherein the body of the first protrusion tapers in a longitudinal direction along the helical thread from the first end to the second end.

2. The medical connector according to claim 1, wherein a radial height of the first protrusion at the first end is greater than the radial height of the first protrusion at the second end.

3. The medical connector according to claim 1, further comprising a second protrusion extending radially outward from the sidewall of the body of the medical connector.

4. The medical connector according to claim 3, wherein a circumferential length of the first protrusion is longer than a circumferential length of the second protrusion.

5. The medical connector according to claim 3, wherein the second protrusion includes a first end and a second end, a radial height of the second protrusion at the first end is greater than the radial height of the second protrusion at the second end.

6. The medical connector according to claim 5, wherein an axial width of the second protrusion is larger at the first end than the axial width of the second protrusion at the second end.

7. The medical connector according to claim 3, wherein the first protrusion and the second protrusion are substantially aligned in a longitudinal direction of the body.

8. The medical connector according to claim 3, wherein the second protrusion has a body that defines a generally teardrop-shaped circumference.

9. The medical connector of claim 3, further comprising a plurality of second protrusions with each second protrusion extending radially outward from the sidewall of the body of the medical connector.

10. The medical connector according to claim 9, wherein the plurality of second protrusions are circumferentially spaced from each other around the body of the medical connector.

11. The medical connector according to claim 1, wherein the body of the first protrusion defines a generally teardrop-shaped circumference.

12. The medical connector according to claim 1, further comprising a plurality of first protrusions with each first protrusion extending radially outward from the crest portion of the helical thread.

13. The medical connector according to claim 12, wherein the plurality of first protrusions are circumferentially spaced from each other around the body of the medical connector.

14. A method of connecting two fluid containers comprising:
 providing a first fluid container comprising a connector having a helical thread extending radially outward from a surface of the connector, and providing a second fluid container comprising a mating connector comprising a helical thread extending radially outward from a surface of the mating connector, the connector of the first fluid container including at least one micro-thread extending radially outward from a root portion of the helical thread;
 engaging the helical thread of the mating connector with the helical thread of the connector;
 advancing the mating connector onto the connector by rotating the mating connector; and
 engaging the at least one micro-thread with the mating connector such that the friction between the connector and the mating connector is increased when the at least one micro-thread of the connector contacts the helical thread of the mating connector as the mating connector is advanced onto the connector,
 wherein the connector comprises more than one micro-thread and each micro-thread is sized and positioned such that the increase in friction provided by contact with each successive micro-thread is greater than the increase in friction provided by a previously contacted micro-thread, and wherein a first micro-thread that first contacts the helical thread of the mating connector has a smaller surface area than a second micro-thread that is subsequently contacted by the helical thread of the mating connector as the mating connector is advanced on the connector.

15. The method according to claim 14, further comprising:
engaging a stop with the mating connector to stop advancement of the mating connector onto the connector.

* * * * *